United States Patent [19]

Matsumoto et al.

[11] Patent Number: 5,412,111

[45] Date of Patent: May 2, 1995

[54] METHOD OF PREPARING (3R,4R)-3-HYDROXY-4-HYDROXYMETHYL-4-BUTANOLIDE

[75] Inventors: Katsuya Matsumoto; Takashi Ebata; Koshi Koseki; Koji Okano; Hiroshi Kawakami; Hajime Matsushita, all of Yokohama, Japan

[73] Assignee: Japan Tobacco Incorporated, Tokyo, Japan

[21] Appl. No.: 95,182

[22] Filed: Jul. 23, 1993

[30] Foreign Application Priority Data

Jul. 23, 1992 [JP] Japan ................................ 4-197008

[51] Int. Cl.⁶ ........................................... C07D 307/33
[52] U.S. Cl. .................................................. 549/313
[58] Field of Search ...................................... 549/313

[56] References Cited

FOREIGN PATENT DOCUMENTS 0460413 12/1991 European Pat. Off. .
61-65878 4/1986 Japan .

OTHER PUBLICATIONS

"Structural and Stereoisomeric Specificity of Serum-Borne Sugar Acids Related to Feeding Control by Rats" by T. Sakata, *Brain Research Bulletin*, vol. 25, 969–974 (1990).

"Methyl 5-0-Tert-Butyldiphenylsilyl-2-Deoxy-αβ-D-Threo-Pentofuranoside As A Divergent Intermediate for the Synthesis of 3'-Substituted-2', 3'-Dideoxynucleosides: Synthesis of 3'-Azido-3'-Deoxythymidine, 3'-Deoxy-3'-Fluorothymidine and 3'-Cyano-3'-Deoxythymidine" to G. Fleet et al., *Tetrahedron*, 44, 625 (1988).

"Reaction of Aldehydes with Stabilized Sulfur Ylides, Highly Stereoselective Synthesis of 2,3-Epoxy-amides" to M. Fernandez et al., *Tetrahedron*, vol. 46, No. 23, pp. 7911–7922, 1990.

"Halogenated Enolates. Synthesis of 2-Deoxypentose Derivatives from D-Glyceraldehyde" by B. Rague et al., J. Chem. Soc. Perkin Trans. I, 1982.

"Reaction of Methyl Diazoacetate with 2,3 Q-Isopropylidene-D-Glyceraldehyde. Stereoselectivity in the Synthesis of 2-Deoxy-D-Aldonates and 2-Deoxy-γ,D-Aldonolactones", F. J. Lopez-Herrera et al., *Tetrahedron*, vol. 46, No. 20, pp. 7165–7174 (1990).

(List continued on next page.)

*Primary Examiner*—C. Warren Ivy
*Assistant Examiner*—Ba K. Trinh
*Attorney, Agent, or Firm*—Birch, Stewart, Kolasch & Birch

[57] ABSTRACT

Providing a method of preparing (3R,4R)-3-hydroxy-4-hydroxymethyl-4-butanolide conveniently and selectively from a widely available raw material in a high yield. A carbonyl group of the 2-position of levoglucosenone is reduced to obtain a hydroxyl group of a β-configuration. Then, an iodo-group of an α-configuration and an acyloxy ion of a β-configuration are introduced regioselectively and stereoselectively to the double bond at the 4-position and the 3-position of the above-mentioned levoglucosenone, respectively, keeping a trans stereochemical relationship. An alkoxide is then formed, by hydrolysis and an oxirane ring of a β-configuration is formed by removing an iodo-group by intramolecular nucleophilic displacement reaction of the alkoxide. After the hydroxyl group of the 2-position is oxidized to convert to a carbonyl group, the oxirane ring is reductively and selectively cleaved, thereby obtaining a chemical compound having no substituent at the 3-position and a hydroxyl group of a β-configuration at the 4-position. Finally a lactone of 5-membered-ring is prepared by subjecting the above-obtained compound to Baeyer-Villigar oxidation.

12 Claims, No Drawings

OTHER PUBLICATIONS

"Optisch Aktive C$_5$-Bausteine zur Synthese von Naturlich Vorkommenden Terpenen" by R. Dumont et al., *Helvetica Chimica Acta,* vol. 66, Fac. 3 (1983).

"Efficient Synthesis of (S)-5-Hydroxymethyl-5(-H)-Furan-2-One From D-Mannitol" by G. A. Danilova et al., *Tetrahedron Letters,* vol. 27, No. 22, pp. 2489-2490, 1986.

"The Preparation of Some Bromodeoxy-and Dibromodideoxy-Pentonolactones" by K. Bock et al., *Carbohydrate Research,* 90 (1981) pp. 17-26.

"Synthesis of Some Esters and Lactones of Aldonic Acids" by W. Humphlett, *Carbohydrate Research,* 4, 157-164 (1967).

"Some Reactions of Levoglucosenone" by F. Shafizadeh et al., *Carbohydrate Research,* 71 (1979) 169-191.

"Advanced Organic Chemistry, Third Edition", J. March, 1985, pp. 1081-1083.

"Advanced Organic Chemistry, Third Edition", J. March, 1985, pp. 732-734.

"Reduction of α,β-Oxido Ketones with Chromous Acetate. Synthesis of 3β,5β,17β,19-Tetrahydroxy-5-β-androstane, a Degradation Product of Strophanthidin" by C. H. Robinson et al, *Journal of Organic Chemistry,* vol. 37, No. 4, 1972, pp. 565-568.

METHOD OF PREPARING (3R,4R)-3-HYDROXY-4-HYDROXYMETHYL-4-BUTANOLIDE

BACKGROUND OF THE INVENTION

1. Field of the Invention

The present invention relates to a process of preparing (3R,4R)-3-hydroxy-4-hydroxymethyl-4-butanolide.

2. Description of the Related Art

In recent years, chemical compounds containing natural occurring sugar and sugar-analog compounds have been drawn attention as useful physiologically active ingredients in a fine chemical field such as pharmaceutical agents and agricaltural agents. Many studies have been widely conducted on synthesis of the above-mentioned chemical compounds.

Examples of the above-mentioned compounds include hydroxylactone and the like which are not only physiologically active compounds but also sugar-analog compounds to be used as starting materials for various useful chemical compounds.

(3R,4R)-3-hydroxy-4-hydroxymethyl-4-butanolide represented by the following formula [1] is a chemical compound belonging to hydroxylactones and a noteworthy compound by virtue of to its usefulness.

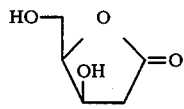

[1]

Basic physiological studies with regard to physiological properties of the above-mentioned lactone have been conducted since the lactone is expected to be used as an appetite suppressing ingredient (an appetite satisfying ingredient) and application of the lactone to pharmaceutical agents and agricultural agents has been desired [T. Sakata, Brain Res. Bull., 25(6), 969–74, (1990)]. On the other hand, the lactone is also useful as a starting material for synthesis of other useful chemical compounds. For example, 2-deoxy-D-lyxose known as a rare sugar compound can be obtained by a process in which lactol is formed by reduction of a carbonyl group of the 1-position of the lactose. Thus obtained rare sugar can be used as a raw material of a sugar part of AZT (3'-azido-3'-deoxythymidine), which is a nucleic acid derivative known as an anti-AIDS drug [G. W. J. Fleet, J. C. Son, and A. E. Derome, Tetrahedoron, 44, 625, (1988)]. The lactone can be used as an aroma, for example, as an additive to improve aroma and taste of cigarettes. The lactone can be further used as a starting material for synthesizing other aromas (Published Patent "5-O-substituted-2-deoxyxylono-1,4-lactone and a process of preparing the same", Published Unexamined Japanese Patent Application No. 61-65878).

As described above, (3R,4R)-3-hydroxy-4-hydroxymethyl-4-butanolide is a useful hydroxylactone expecting a wide range usage. However, the lactone is rarely obtained from natural source so as to totally depend on synthetic methods.

There are five representative conventional methods.

1) 2,3-O-isopropylidene-D-glyceraldehyde is reacted with enolate prepared by trihalogenoacetate and Grignard reagent, thereby to increase carbon numbers of the glyceraldehyde. Then, lactone is synthesized through a process of dehalogenation etc. This method includes four processes and an overall yield is 16% [B. Rague, Y. Chapleur, and B. Castro, J. Chem. Soc. Perkin Trans. I, 2063, (1982)].

2) 2,3-O-isopropylidene-D-glyceraldehyde is reacted with sulfanylidene derivative (Me$_2$S=CHCONR$_2$) which is sulfurylide, thereby to increase carbon numbers of glyceraldehyde. The resultant product, 2,3-epoxyamide is then subjected to reductive ring-opening, followed by lactonization. This method includes three processes and an overall yield is about 10% [M. V. Fernandez, P. D. Lanes, and F. J. L. Herrera, Tetrahedron, 46, 7911, (1990)].

3) 2,3-O-isopropylidene-D-glyceraldehyde is reacted with diazoacetate, thereby to increase carbon numbers of the glyceraldehyde. The resultant product β-ketoester and 2-diazo-3,4,5-trihydroxypentanoate derivative are subjected to a reduction reaction, followed by lactonization. This method includes three processes and an overall yield is 12 to 16% [F. J. L. Herrera, M. V. Fernandez, and S. G. Claros, Tetrahedron, 46, 7165 (1990)].

4) 2,3-O-isopropylidene-D-glyceraldehyde is reacted with organic lithium reagent (LiCH$_2$COOBu-t), thereby to increase carbon numbers of glyceraldehyde. The resultant product, 3,4,5-trihydroxypentanoate is subjected to lactonization [G. A. Danilova, V. I. Mel'nikova, and K. K. Pivnitsky, Tetrahedron Lett., 27, 2489 (1986)].

5) D-galactose is treated with alkali under high pressure to obtain D-lyxono-1,4-lactone. The resultant product lactone is subjected to bromination and debromination of the 2-position thereof, thereby to obtain a desired lactone which is a deoxy from at the 2-position. This method includes 4 processes and an overall yield is 38% or less [K. Bock, I. Lundt, and C. Pedersen, Carbohydr. Res., 90, 17, (1981); and W. J. Humphlett, Carbohydr. Res., 4, 157, (1967)].

The above methods 3) and 4) have low yields of (3R,4R)-3-hydroxy-4-hydroxymethyl-4-butanolide since an intermediate compound having a desired configuration is rarely obtained due to low stereoselectivity of a hydroxyl group formed at the 3-position by an increasing-carbon-number reaction of 2,3-O-isopropylidine-D-glyceraldehyde. This process further requires additional two processes to obtain a raw material of 2,3-0-isopropylidene-D-glyceraldehyde from D-mannitol with the result that a yield is further decreased [R. Dumont and H. Pfander, Helv. Chim. Acta, 66, 814, (1983)].

In the method 4), on the other hand, 3-hydroxy-4-hydroxymethyl-4-butanolide is synthesized as a synthetic intermediate. Therefore, stereoselectivity of a hydroxyl group of the 3-position of the above compound is not a matter of consideration. Since a diastereoisomer simultaneously produced at the 3-position of the above compound is difficult to separate, the next reaction is carried out without separating the diasteroisomer. In process 5), 3-hydroxy-4-hydroxymethyl-4-butanolide is used as an synthetic intermediate. As s result, a reaction is proceeded without diastereoisomer isolation. Process 5) is difficult to operate since high pressure is required as a reaction condition. Therefore, it is very difficult to selectively obtain (3R,4R)-3-hydroxy-4-hydroxymethyl-4-butanolide.

As is apparent from the foregoing, a convenient synthetic method has not been attained to prepare the desired compound of the present invention with a high stereoselectivity in a high yield.

SUMMARY OF THE INVENTION

The present invention has been developed on the basis of the above-mentioned circumstances. The object of the present invention is to provide a method of preparing (3R,4R)-3-hydroxy-4-hydroxymethyl-4-butanolide from a widely available raw material conveniently and selectively in a high yield.

The present inventors have conducted intensive and extensive studies and found an effective method of preparing (3R,4R)-3-hydroxy-4-hydroxymethyl-4-butanolide in an overall yield of as high as 42.3% using levoglucosenone as a starting material which is obtained from cellulose by means of thermolysis. The novel method comprises 5 processes which is less than that of a convenient method.

That is, the present invention provides a method of preparing (3R,4R)-3-hydroxy-4-hydroxymethyl-4-butanolide represented by the following formula [1] using levoglucosenone as a starting material which is represented by the following formula [2] and comprising the following processes (a) to (e).

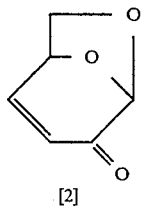   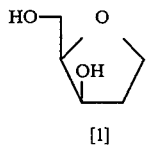

[2]   [1]

(a) a process of preparing a chemical compound represented by formula [3] having a hydroxyl group of a β-configuration by reducing a carbonyl group of the 2-position of the compound represented by formula [2] as shown in below:

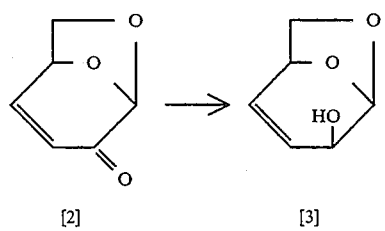

[2]   [3]

(b) a process of preparing a chemical compound represented by formula [4] by reacting the chemical compound represented by formula [3] with iodine and a chemical compound containing an acyloxy ion, followed by hydrolysis as shown in below:

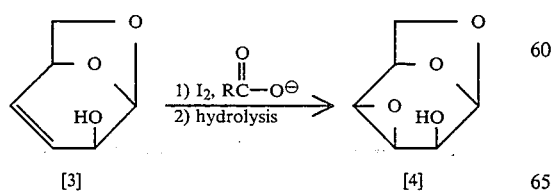

[3]   [4]

(c) a process of preparing a carbonyl compound represented by formula [5] by oxidizing a hydroxyl group of the 2-position of the chemical compound represented by formula [4] as shown in below:

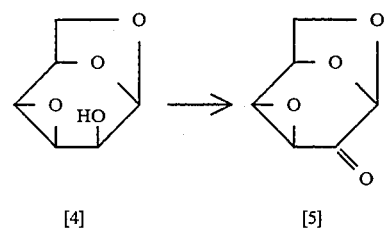

[4]   [5]

(d) a process of preparing a chemical compound represented by formula [6] by a ring-opening reaction of an oxirane ring of the chemical compound [5] as shown in below:

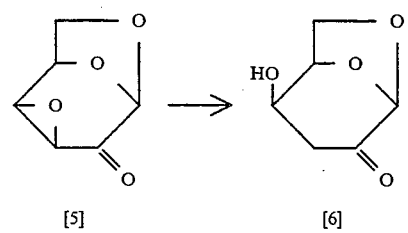

[5]   [6]

(e) a process of preparing (3R,4R)-3-hydroxy-4-hydroxymethyl-4-butanolide represented by the following formula [1] by subjecting the chemical compound represented by formula [6] to Baeyer-Villiger oxidation as shown in below:

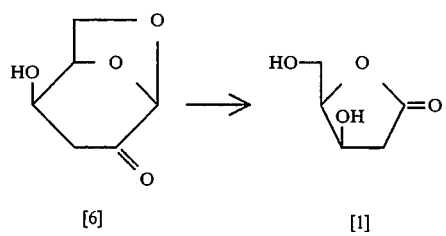

[6]   [1]

To be more specific, the present invention provides a method comprising that process (b) in said (a) to (e) is the following step.

Process (b): An iodo-group of an α-configuration is added to the double bond at 4-position of a compound represented by formula [3] and an acyloxy ion of a β-configuration is added to the double bond at 3-position of a compound represented by formula [3] in a trans form, followed by subjecting an acyloxy group to hydrolysis in the presence of a base, thereby to regioselectively and stereoselectively prepare the chemical compound represented by formula [4] having an oxirane ring of a β-configuration.

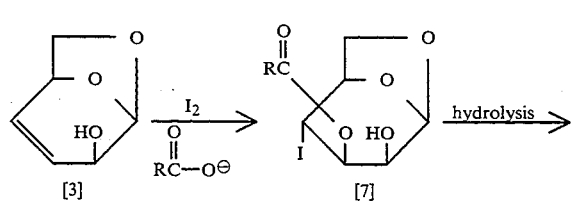

[3]   [7]

-continued

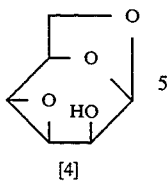

[4]

where R is an alkyl group or an aryl group.

Furthermore, the present invention provides a method comprising processes (a) to (e), in which a chemical compound represented by the following formula [5'9 is obtained by hydration of the produced chemical compound represented by formula [5] in process (c). The present invention still provides a process comprising processes (a) to (e) in which a chemical compound represented by the following formula [6'] is obtained by hydration of a produced chemical compound represented by formula [6'] in process (d).

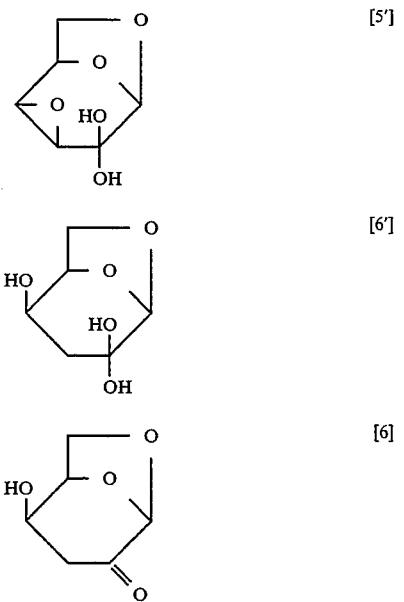

DESCRIPTION OF THE INVENTION

Hereinafter the method of preparing (3R,4R)-3-hydroxy-4-hydroxymethyl-4-butanolide [1] of the present invention will be described in more detail step by step from processes (a) to (e).

Process (a) is a process of preparing 1,6-anhydro-3,4-dideoxy-$\beta$-D-threo-hex-3-enopyranose [3] having a hydroxyl group of a $\beta$-configuration by reducing a carbonyl group of the 2-position of levoglucosenone represented by formula [2]. The reaction of the above process is performed by use of a reducing agent such as lithium aluminum hydride or sodium borohydride in an appropriate solvent such as diethyl ether and tetrahydrofuran.

A process (b) is a process of preparing a chemical compound [4] having an oxirane ring of a $\beta$-configuration from 1,6-anhydro-3,4-dideoxy-$\beta$-D-threo-hex-3-enopyranose [3] obtained in the process (a). This process is performed as described hereinbelow. First, an acyloxyl group of a $\beta$-configuration is added to the 3-position of a chemical compound [3] and an iodogroup of an $\alpha$-configuration is added to the 4-position of a chemical compound [3] in a trans form, thereby to obtain a chemical compound [7].

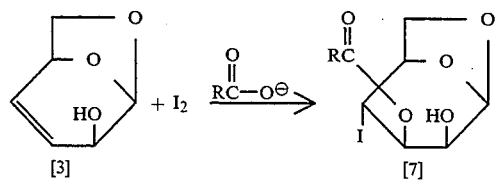

where R is an alkyl group or aryl group.

The above reaction is performed in an appropriate solvent by use of no less than 1 equivalent of iodine relative to a double bond of the chemical compound [3] and no less than 1 equivalent of a carboxylic acid or a metal carboxylate.

The solvent of the above reaction is not restricted except water, alcohols, or those which release water and alcohols by hydrolysis. Preferably, a carboxylic acid, hexane, acetonitrile, and the like are used. More preferably, a carboxylic acid itself is used as a solvent when the carboxylic acid is used as a solvent, any type of carboxylic acid can be used as long as it is a liquid state under the reaction condition. Preferably, acetic acid, propionic acid, butyric acid, and the like are used. Most preferably, acetic acid is used.

The metal carboxylate is not restricted as long as it assist to generate an iodonium ion from iodine. For Example, silver carboxylate and cesium carboxylate can be used. More specificity, silver acetate, silver benzoate, cesium acetate, and the like are used. The metal carboxylate is not required when a carboxylic acid is added to the reaction system (including the case a carboxylic acid is used as a solvent), however, if a metal carboxylate is added thereto, a yield of a product can be improved. In the case that a carboxylic acid is not added to the reaction system, a metal carboxylate is required.

The reaction temperature and time period is not restricted, generally, the above reaction is performed at room temperature in a time period of one hour to 10 days.

Second, the obtained chemical compound [7] is hydrolyzed to form alkoxide at the 3-position. An iodo-group of the 4-position is removed by intramolecular nucleophilic displacement reaction of the alkoxide, thereby to obtain an oxirane ring of a $\beta$-configuration.

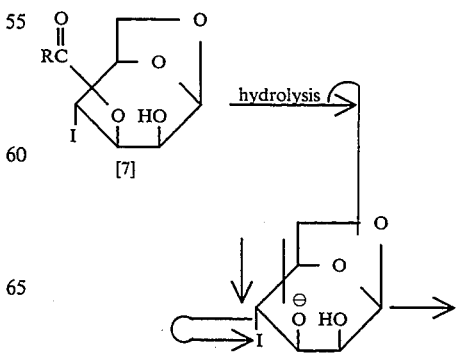

-continued

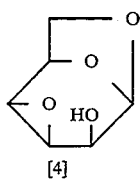

[4]

A base used in the hydrolysis is not particularly restricted. In general, any base used for removing an acyl group can be used. Examples of the base are alkali hydroxide such as sodium hydroxide and potassium hydroxide; alkali carbonate such as sodium carbonate, and potassium carbonate; metal alkoxide such as sodium methoxide and potassium butoxide; ammonia water, and the like.

The solvent of the above reaction is not restricted as long as it is used in a general hydrolysis. In general, water and an organic solvent such as methanol and ethanol can be used.

Process (c) is a process in which the chemical compound [4] obtained in process (b) is oxidized to obtain a chemical compound [5] having a carbonyl group at the 2-position. The oxidation method used in this process is not restricted as long as a hydroxyl group can be converted to a carbonyl group by oxidation without cleaving an oxirane ring. There are many oxidation methods. Representative examples of the oxidation methods are the following 1) to 7).

1) The oxidation with dimethyl sulfoxide in combination with dicyclohexylcarbodiimide, acetic anhydride, phosphorous pentoxide, trifluoroacetic anhydride, oxalyl chloride, halogen, and the like.
2) The oxidation with chromate such as chromium oxide (VI) represented by John's oxidation, dichromate, chromium oxide-pyridine complex (Collins reagent), pyridinium chlorochromate (PCC), pyridinium dichromate (PDC), and the like.
3) The oxidation with manganese dioxide.
4) The oxidation with hypohalite, halic acid, and the like.
5) The oxidation with Oppenauer oxidation or 2,3-dichloro-5,6-dicyano-p-benzoquinone.
6) The oxidation with a transition metal catalyst such as ruthenium tetraoxide, a platinum catalyst, and a palladium catalyst.
7) The oxidation with silver carbonate, copper (II) salt, lead tetraacetate, and the like.

The reaction conditions including the amount of reagents, the type of solvent, temperature, and time period are not restricted since the reaction condition varies depending on individual oxidation reactions. A reaction condition suitable for an individual oxidation reaction can be chosen.

A carbonyl group of the 2-position of the chemical compound represented by formula [5] obtained in the above-mentioned oxidation reaction may be acceptable if it is obtained in a form of geminal-diol (a chemical compound [5']) as a result of hydration. The carbonyl group of the compound [5] may be positively hydrated under an appropriate condition to obtain a chemical compound [5']. The condition of the hydration is not restricted. For Example, the hydration is performed by treating the compound [5] in a solvent containing water such as acetonitrile-water or tetrahydrofuran-water. It may be more effective if the compound [5] is hydrated in the presence of an acid catalyst such as acetic acid and p-toluenesulfonate.

Process (d) is a process, in which an oxirane ring of the compound [5] obtained in process (c) is reductively cleaved and convert regioselectively to a chemical compound [6] having a hydroxyl group of a $\beta$-configuration at the 4-position and no substituent at the 3-position. This process can be also applied to the geminal-diol complex [5'] obtained by hydration of the compound [5].

The selective reductive ring cleavage reaction of an oxirane ring used in this step is not restricted as long as it converts $\alpha$, $\beta$-epoxyketone to $\beta$-hyrdoxyketone. Specially, a method using sodium phenylselenotrialkoxyborate as a reducing agent is effective. The reducing agent can be generated in situ by treatment of diphenyl diselenide with sodium borohydride in an alcohol solvent.

This reaction may be performed under the condition in which no less than 0.5 equivalent of diphenyl diselenide and no less than 1 equivalent of sodium borohydride are used. Preferably, 0.1 to 1 equivalent of acetic acid is added thereto. As a solvent used in the above reaction, an alcohol solvent such as ethanol and isopropyl alcohol is suitable. The reaction temperature is not restricted but preferably the reaction is performed in an ice-cold condition. The reaction time is approximately 1 to 10 hours.

Other selective reduction method of the oxirane ring is performed by use of zinc, chromium (II) acetate sodium iodide, and the like.

Geminal-diol of the 2-position of the compound [6'] obtained when the compound [5'] is used as a starting material in this process should be converted to a carbonyl group by dehydration by use of appropriate dehydrating agent prior to next process (e).

Process (e) is a process in which the compound [6] obtained in process (d) is subjected to Baeyer-Villigar oxidation to give a lactone compound having 5-membered ring, i.e., (3R,4R)-3-hydroxy-4-hydroxymethyl-4-butanolide [1].

The oxidizing agent used in this step is not restricted as long as it is usually used in the 10 Baeyer-Villigar oxidation. Peracetic acid and metachloroperbenzoic acid are preferably used. These oxidation agents are preferably used in an amount of 1 to 10 equivalents to the compound [6]. The organic solvent used in this process is not restricted as long as it is inert in Baeyer-Villigar oxidation. For example, acetic acid and methylene chloride can be used as the solvent. The reaction is preferably performed at around room temperature in the time period of 10 minutes to 10 hours.

After a completion of the reaction, an excess amount of peracid should be consumed by adding dimethyl sufide and the like to perform a next process safely.

Since the hydroxyl group of a produced compound can be partly converted to folmyl ester, the produced compound is preferably hydrolyzed by treatment under an acidic condition. The acid used in the hydrolysis is not restricted as long as it is a general acid catalyst such as hydrochloric acid, sulfuric acid, and Amberlite IR-120B (a proton type). Any solvent such as water and alcohols used in a general acid hydrolysis can be used. The temperature is not restricted as long as it is within a range of 0 to 100° C. Preferably room temperature is used. As a reaction time, a time period of 1 to 20 hours is preferable.

Through the above-mentioned processes (a) to (e), (3R,4R)-3-hydroxy-4-hydroxymethyl-4-butanolide represented by formula [1] can be obtained.

DETAILED DESCRIPTION OF THE PREFERRED EMBODIMENT

[Examples]

Hereinafter, the present invention will be described in detail with reference to the following Examples which should not be construed as limiting the scope of the present invention.

Example 1

Process (a): Synthesis of 1,6-anhydro-3,4-dideoxy-$\beta$-D-threo-hex-3-enopyranose 2.42 g (63.8 mmol) of lithium aluminum hydride was suspended in 200 ml of dry ether. 7.98 g (63.3 mmol) of levogluconenone dissolved in 130 ml of dry ether was added dropwise to the suspension solution under a nitrogen atmosphere while ice-cooling. Then, the reaction mixture was stirred at room temperature for one hour and 4.60 g (256 mmol) of water was added thereto. After further methanol was added and undissolved material was filtered off, the solvent was removed from the filtrate under reduced pressure. The residue was purified by means of silica gel column chromatography (hexane: diethyl ether=1:1-1:2). The obtained product was recrystallized from hexane-diethyl ether mixed solvent (hexane: diethyl ether=4: 1), thereby obtaining 5.70 g (yield: 70.3%) of 1,6-anhydro-3,4-dideoxy-$\beta$-D-threo-hex-3-enopyranose represented by the following formula [3].

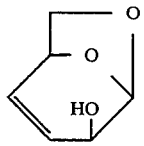
[3]

Melting Point 65.6°–66.4° C.
$[\alpha]^{25}D - 30.3°$ (c 1.00, CHCl$_3$)
IR V$_{max}$ 3412 (br), 3050 (w), 1425 (m), 1259 (m), 1180 (m), 1125 (s), 1071 (s), 1046 (s)
$^1$H-NMR (CDCl$_3$, ppm from TMS) 6.12 (1H, dd, J=9.9, 4.2 Hz); the 4-position,
5.72 (1H, ddd, J=9.9, 2.2, 2.2 Hz); the 3-position 5.52 (1H, b); the 1-position 4.67 (1H, dd, J=4.2, 4.1 Hz); the 5-position 4.34 (1H, m); the 2-position 3.84 (1H, d, J=6.6 Hz); the 6'-position 3.78–3.74 (1H, dd, J=6.6, 4.1 Hz); the 6-position 2.10 (1H, d, J=12.0 HZ); OH.

Process (b): Synthesis of 1,6:3,4-dianhydro-$\beta$-D-talopyranose 0.13 g (1.00 mmol) of 1,6-anhydro-3,4-dideoxy-$\beta$-D-threo-hex-3-enopyranose represented by the above formula [3] was dissolved in 4.6 ml of acetic acid, and further 0.33 g (2.00 mmol) of silver acetate was added thereto. While vigorously stirring the solution at room temperature, 0.27 g (1.05 mmol) of iodine was gradually added to the solution. After the reaction mixture was stirred for 5 hours at room temperature under a nitrogen atmosphere, 40 ml of 25% ammonia water was gradually added to the solution while ice-cooling to convert it to a basic solution. Further 40 ml of methanol was added to the basic solution, which was stirred for overnight at room temperature. Undissolved material was filtered off, and the solvent was removed from the filtrate under reduced pressure. The residue was purified by means of silica gel column chromatography (hexane: ethyl acetate=1: 1), thereby obtaining 1.09 g (yield: 93.8%) of 1,6:3,4-dianhydro-$\beta$-D-talopyranose represented by the following formula [4]. This was recrystallized from a hexane-diethyl ether mixed solvent (hexane:diethyl ether=1:4).

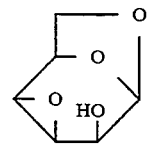
[4]

Melting Point: 74.0°–75.2° C.
$[\alpha]^{24}D - 49.7°$ (c 1.44, H$_2$O)
$^1$H-NMR (CDCl$_3$, ppm from TMS): 5.30 (1H, d, J=3.8 Hz); the 1-position, 4.82 (1H, dd, J=4.7, 4.7 Hz); the 5-position, 3.95 (1H, d, J=6.6 Hz); the 6-position, 3.83–3.76 (2H, m); the 2- and 4-position, 3.56 (1H, dd, J=6.6, 4.7 Hz); the 6'-position 3.34 (1H, ddd, J=3.9, 3.9, 1.0 Hz); the 3-position 2.41 (1H, d, J=12,2 Hz); OH.
$^{13}$C-NMR [CDCl$_3$, ppm from CDCl$_3$ (77.4 ppm)]: 98.2, 72.1, 68.9, 64.3, 57.6, 50.6.

Process (c): Synthesis of 1,6:3,4-dianhydro-$\beta$-D-lyxo-hexopyranos-2-ulose 1.05 ml (12.22 mmol) of oxalyl chloride was dissolved in 70 ml of dry methylene chloride and 1.86 ml (26.19 mmol) of dimethyl sufoxide dissolved in 17 ml of dry methylene chloride was added dropwise thereto at −70° C. under a nitrogen atmosphere. After the mixture was stirred for 2 minutes, 1.68 g (11.66 mmol) of 1,6:3,4-dianhydro-$\beta$-D-talopyranose represented by the above formula [4] dissolved in 35 ml of a dry methylene chloride was added dropwise to the reaction mixture. Further stirred for 15 minutes, 8.16 ml (57.51 mmol) of triethylamine was added to the reaction solution and stirred for 5 minutes. Then, a temperature was raised to room temperature and the solvent was removed from the reaction mixture under reduced pressure. Thereafter, the residue was purified by means of silica gel column chromatography (hexane: ethyl acetate=1:3), thereby obtaining 1.64 g (yield: 87.9%) of 1,6:3,4-dianhydro-$\beta$-D-lyxo-hexopyranos-2-ulose represented by the following formula [5]. This was recrystallized from a hexane-ethyl acetate mixed solvent as a hydrate represented by the following [5'].

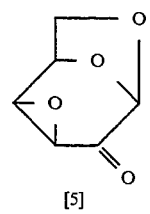 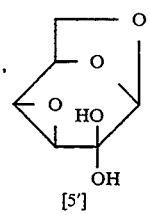
[5]  [5']

Melting Point: 106°–110° C.
$[\alpha]^{26}D - 48.2°$ (c 0.20, CHCl$_3$)
$^1$H-NMR (CDCl$^3$—CD$_3$OD, ppm from TMS): 5.04 and 4.94 (1H, b); the 1-position, 4.86 and 4.85 (1H, dd, J=4.8, 4.6 Hz); the 5-position, 3.99 and 3.97 (1H, d, J=6.6 Hz); the 6-position, 3.72–3.71 (1H, dd, J=4.6, 4.5 Hz); the 4-position, 3.56 (1H, dd, J=6.6, 4.8 Hz); the 6'-position 3.23 and 3.16 (1H, dd, J=4.5 2.0 Hz); the 3-position Process (d): Synthesis of 1,6-anhydro-3-deoxy-β-D-threo-hexopyranos-2-ulose 0.47 g (1.50 mmol) of diphenyl diselenide dissolved in 7.5 ml of dry ethanol and 0.11 g (3.00 mmol) of sodium borohydride was gradually added thereto at room temperature. After the reaction mixture was stirred for 5 minutes, 11.6 ml of acetic acid was added to the reaction mixture while ice-cooling. Then, 0.16 g (1.00 mmol of 1,6:3,4-dianhydro-β-D-lyxo-hexopyranos-2-ulose monohydrate represented by the above formula [5'] dissolved in 8 ml of a dry ethanol was added dropwise thereto. After the reaction mixture was stirred for 2 hours while ice-cooling, a temperature thereof was raised to room temperature and diluted by adding 78 ml of ethyl acetate. After a solvent was removed from the reaction solution under reduced pressure, the residue was purified by means of silica gel column chromatography (hexane: ethyl acetate=1:2), thereby obtaining 0.12 g (yield: 80.6%) of 1,6-anhydro-3-deoxy-β-D-threo-hexopyranos-2-ulose represented by the following formula [6]. This was recrystallized from a hexane-diethyl ether mixed solvent.

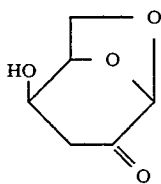

[6]

Melting Point: 49.0°–50.5° C.
$[\alpha]_{26}D -218.0°$ (c 1.0, CHCl$_3$)
$^1$H-NMR (CDCl$_3$, ppm from TMS): 5.06 (1H, s); the 1-position, 4.59 (1H, ddd, J=4.9, 4.0, 0.7 Hz); the 5-position, 4.42 and 4.34 (1H, m); the 4-position, 4.37 (1H, dd, J=8.0, 0.7 Hz); 3.90(1H, ddd, J=8.0, 4.9, 0.5 Hz) the 6-position, 2.77 (1H, dddd, J=15.8, 6.8, 1.6, 1.2 Hz); 2.52 (1H, dd, J=15.8, 9.8 Hz), the 3-position, 2.67 (1H, J=4.4 Hz); OH Process (e): Synthesis of (3R,4R)-3-hydroxy-4-hydroxymethyl-4-butanolide 1.58 g (10.95 mmol) of 1,6-anhydro-3-deoxy-β-D-threo-hexopyranos-2-ulose represented by the above formula [6] was dissolved in 20 ml of acetic acid. 7 ml of 40% of peracetic acid was added dropwise to the mixture under a nitrogen atmosphere while ice-cooling. After the reaction mixture was stirred at room temperature for one hour, 5 ml of dimethyl sulfide was gradually added thereto while ice-cooling. After being stirred for one hour at room temperature, a solvent was removed from the reaction solution under reduced pressure. The residue was dissolved in 40 ml of methanol and 1.6 ml of conc. hydrochloric acid was added thereto and then, stirred at room temperature for overnight. A solvent was removed from the reaction solution under reduced pressure and the residue was purified by means of silica gel column chromatography (hexane: ethyl acetate=1:5), thereby obtaining 1.31 g (yield: 90.5%) of (3R,4R)-3-hydroxy-4-hydroxymethyl-4-butanolide by the following formula [1].

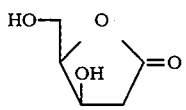

[1]

$[\alpha]^{24}D + 67.3°$ (c 1.01, CH$_3$OH) $^1$H-NMR (CDCl$_3$(CD$_3$)$_2$CO, ppm from TMS): 4.69–4.64 (1H, m); the 3-position, 4.57 (1H, d, J=4.4, Hz); 3-OH, 4.49 (1H, ddd, J=5.3, 5.3, 4.3 Hz); the 4-position, 4.03 (1H, dd, J=6.3, 5.3 Hz); 5-OH 3.94–3.90 (2H, m); the 6-position, 2.85 (1H, dd, J=17.4, 5.9 Hz); 2.42 (1H, dd, J=17.4, 1.8 Hz); the 2-position $^{13}$C-NMR [D$_2$O, ppm from CH$_3$OH (49.8 ppm)]: 179.6, 85.8, 67.9, 59.9, 38.4

Example 2

The reaction was performed by using the same procedure as the above process (d) except that 1,6:3,4-dianhydro-β-D-lyxo-hexopyranos-2-ulose [5] was used instead of a hydrate of 1,6:3,4-dianhydro-β-D-lyxo-hexopyranose-2-urose [5'].

Process (d): Synthesis of 1,6-anhydro-3-deoxy-β-D-threo-hexopyranos-2-ulose 8.90 g (28.5 mmol) of diphenyl diselenide was dissolved in 14.3 ml of dry ethanol and 2.16 g (57.0 mmol) of sodium borohydride was gradually added thereto at room temperature. After the reaction mixture was stirred for 5 minutes, 0.22 ml of acetic acid was added thereto while ice-cooling. Then, 3.04 g (21.09 mmol of 1,6:3,4-dianhydro-β-D-lyxo-hexopyranos-2-ulose [5] dissolved in 152 ml of a dry ethanol was added dropwise thereto. After the reaction mixture was stirred for 2 hours while ice-cooling, a temperature thereof was raised to room temperature and diluted by adding 1,482 ml of ethyl acetate. After a solvent was removed from the reaction mixture under reduced pressure, the residue was purified by means of silica gel column chromatography (hexane: ethyl acetate=1:2), thereby obtaining 1.58 g (yield: 51.9%) of 1,6-anhydro-3-β-D-threo-hexopyranos-2-ulose. Physical properties of this product were consistent with that obtained in process (d) of Example 1.

From the above, according to the present invention, (3R,4R)-3-hydroxy-4-hydroxymethyl-4-butanolide, a kind of hydroxylactone which has been hardly obtained, can be selectively synthesized in a high yield from a starting levoglucosenone through a fewer processes including a reduction of a carbonyl group, an introduction of oxirane ring to a double bond, conversion of a hydroxyl group to a carbonyl group, a reductive ring-opening reaction of the oxirane ring, and Bae-year-villiger oxidation. Owning to this method, (3R,4R)-3-hydroxy-4-hydroxymethyl-4-butanolide which is a raw material for synthesizing various useful compounds can be readily supplied.

What is claimed is:

1. A method of preparing (3R,4R)-3-hydroxy-4-hydroxymethyl-4-butanolide represented by the following formula (1):

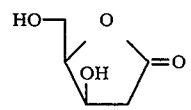

(1)

using levoglucosenone represented by the following formula (2) as a starting material:

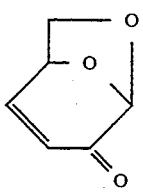

(2)

which comprises:

(a) preparing a chemical compound represented by formula (3) having a hydroxyl group of a β-configuration by reducing a carbonyl group of the 2-position of said compound represented by formula (2) with a metallic hydride reducing agent as shown in the formula reaction:

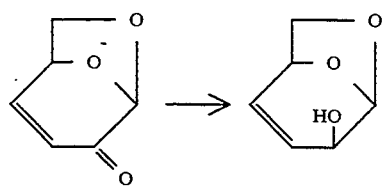

(2)     (3)

(b) preparing a chemical compound represented by formula (4) by reacting said compound represented by formula (3) with iodine and a chemical compound containing an acyloxy ion, followed by hydrolysis as shown in the following reaction:

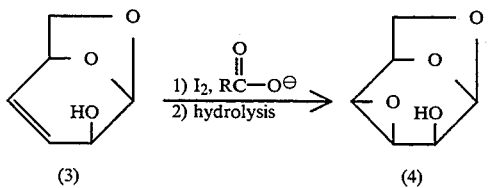

(3)     (4)

(c) preparing a carbonyl compound represented by formula (5) by oxidizing a hydroxyl group of the 2-position of said compound represented by formula (4) with an oxidizing agent selected from the group consisting of dimethyl sulfoxide in combination with dicyclohexylcarbodiimide, acetic anhydride, phosphorous pentoxide, trifluoroacetic anhydride, oxalyl chloride or halogen, chromium oxide (VI), dichromate, chromium oxide-pyridine complex, pyridinium chlorochromate (PCC), pyridinium dichromate (PDC), manganese dioxide, hypohalite, halic acid, 2,3-dichloro-5,6-dicyano-p-benzoquinone, ruthenium tetraoxide, a platinum catalyst, a palladium catalyst, silver carbonate, copper (II) salt, and lead tetraacetate, as shown in the following reaction:

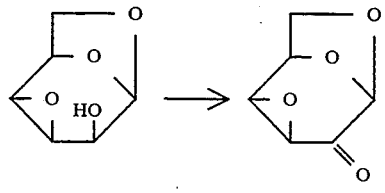

(4)     (5)

(d) preparing a chemical compound represented by formula (6) by a ring-opening reaction of said chemical compound (5) using sodium phenylselenotrialkoxyborate as an agent for performing a reductive ring-opening reaction of an epoxide selectively at an α-position of the carbonyl group of said compound (5) as shown in the following reaction

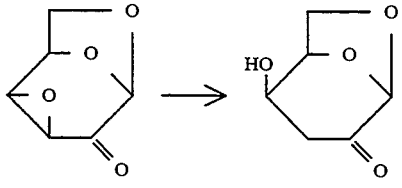

(5)     (6)

and (e) preparing (3R,4R)-3-hydroxy-4-hydroxymethyl-4-butanolide represented by formula (1) by subjecting said chemical compound represented by formula (6) to Baeyer-Villiger oxidation as shown in the following reaction

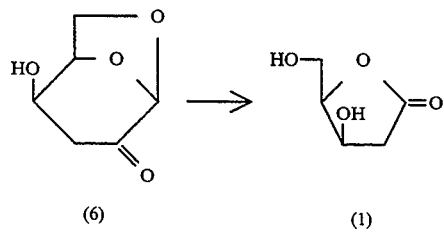

(6)     (1)

2. The method according to claim 1, wherein step (b) is a process in which an iodide group of an α-configuration is added to the double bond at the 4-position of said compound represented by formula (3) and an acyloxy ion of a β-configuration is added to the double bond at the 3-position of said compound represented by formula (3) in a trans form, followed by subjecting an acyloxy group to hydrolysis in the presence of a base, to thereby regioselectively and stereoselectively prepare said compound represented by formula (4) having an oxirane ring of a β-configuration as shown in the following reaction:

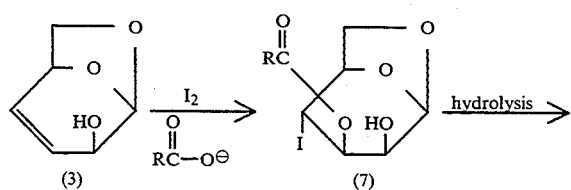

(3)     (7)

-continued

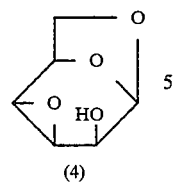

(4)

wherein R is an alkyl group or an aryl group,
and step (d) is a process in which a chemical compound represented by the formula (6) having a hydroxyl group of a β-configuration at the 4-position and no substituent at the 3-position is prepared regioselectively and stereoselectively by reductive ring-opening of an oxirane ring of said compound represented by formula (5).

3. The method according to claim 1 or 2, wherein said prepared compound (5) of step (c) is a hydrate represented by formula (5')

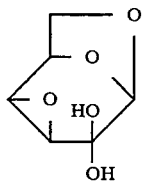

[5']

4. The method according to claim 1 or 2, wherein said prepared product (6) of step (d) is a hydrate represented by formula (6')

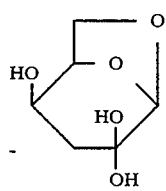

[6']

5. The method according to claim 1, wherein a carbonyl compound represented by formula (5') is prepared in process (c) by oxidizing a hydroxyl group of the 2-position of said compound represented by formula (4) with an oxidizing agent as shown in the following reaction:

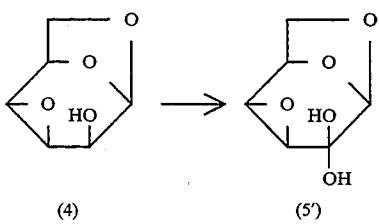

and a chemical compound represented by formula (6) is prepared in process (d) by a ring-opening reaction of said chemical compound (5') using an agent for performing a reductive ring-opening reaction of an epoxide selectively at an α-position of the carbonyl group of said compound (5') as shown in the following reaction:

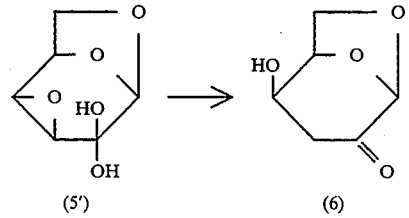

(5')      (6)

6. The method according to claim 1, wherein a carbonyl compound represented by formula (5') is prepared in process (c) by oxidizing a hydroxyl group of the 2-position of said compound represented by formula (4) with an oxidizing agent as shown in the following reaction:

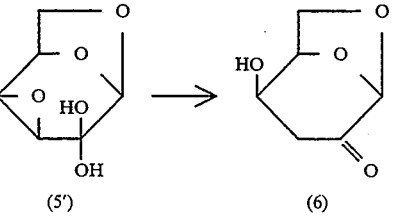

(4)      (5')

and a chemical compound represented by formula (6) is prepared in process (d) by a ring-opening reaction of said chemical compound (5') using an agent for performing a reductive ring-opening reaction of an epoxide selectively at an α-position of the carbonyl group of the compound (5') to obtain a chemical compound represented by the following formula (6'), which is further subjected to dehydration with a dehydrating agent as shown in the following reaction:

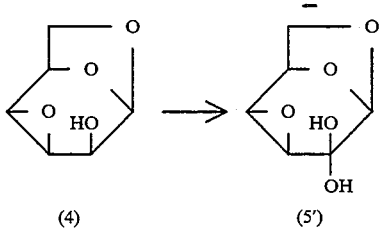

(5')      (6')

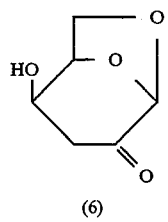

(6)

7. The method according to any one of claims 1, 2, 5 or 6, wherein said chemical compound containing an acyloxy ion is at least one component selected from the group consisting of carboxylic acid and metal carboxylate.

8. The method according to claim 7, wherein said chemical compound containing an acyloxy ion is a carboxylic acid that is also used as a solvent.

9. The method according to claim 7, wherein said carboxylic acid is selected from the group consisting of acetic acid, propionic acid, and butyric acid.

10. The method according to claim 7, wherein said metal carboxylate is selected from the group consisting of silver carbonate and cesium carbonate.

11. The method according to claim 10, wherein said metal carboxylate is selected from the group consisting of silver acetate, silver benzoate, and cesium acetate.

12. The method according to any one of claim 1, 2, 5 or 6, wherein said reducing agent of said process (a) is lithium aluminium hydride.

* * * * *